US010610112B2

(12) United States Patent
Smaill et al.

(10) Patent No.: US 10,610,112 B2
(45) Date of Patent: Apr. 7, 2020

(54) HEART MAPPING SYSTEM (71) Applicants: AUCKLAND UNISERVICES LIMITED, Auckland (NZ); Bruce Smaill, Auckland (NZ); Jichao Zhao, Auckland (NZ); Judit Chamorro Servent, Auckland (NZ); Shu Meng, Auckland (NZ)

(72) Inventors: Bruce Smaill, Auckland (NZ); Jichao Zhao, Auckland (NZ); Judit Chamorro Servent, Auckland (NZ); Shu Meng, Auckland (NZ)

(73) Assignee: Auckland UniServices Limited, Auckland (NZ)

( * ) Notice: Subject to any disclaimer, the term of this patent is extended or adjusted under 35 U.S.C. 154(b) by 119 days.

(21) Appl. No.: 15/552,105

(22) PCT Filed: Feb. 19, 2016

(86) PCT No.: PCT/NZ2016/050024
§ 371 (c)(1),
(2) Date: Aug. 18, 2017

(87) PCT Pub. No.: WO2016/133409
PCT Pub. Date: Aug. 25, 2016

(65) Prior Publication Data
US 2018/0042491 A1 Feb. 15, 2018

Related U.S. Application Data (60) Provisional application No. 62/118,395, filed on Feb. 19, 2015.

(30) Foreign Application Priority Data

Feb. 19, 2015 (NZ) .......................... 705231

(51) Int. Cl.
A61B 5/042 (2006.01)
A61B 5/0215 (2006.01)
(Continued)

(52) U.S. Cl.
CPC .......... *A61B 5/0215* (2013.01); *A61B 5/0044* (2013.01); *A61B 5/042* (2013.01);
(Continued)

(58) Field of Classification Search
CPC ..... A61B 5/0044; A61B 5/042; A61B 5/0422; A61B 5/6852; A61B 18/1492
See application file for complete search history.

(56) References Cited

U.S. PATENT DOCUMENTS 7,729,752 B2 6/2010 Harlev et al.
8,401,625 B2 3/2013 Harlev et al.
(Continued)

FOREIGN PATENT DOCUMENTS

WO WO-2016133409 8/2016

OTHER PUBLICATIONS

"International Application No. PCT/NZ2016/050024, International Preliminary Report on Patentability dated Aug. 22, 2017", (Aug. 22, 2017), 11 pgs.
(Continued)

Primary Examiner — Tammie K Marlen
(74) Attorney, Agent, or Firm — Schwegman Lundberg & Woessner, P.A.

(57) ABSTRACT

A method of determining physiological information for an internal body surface using an open catheter comprising multiple sensors. Sensor potentials are obtained and used to determine catheter potentials within the catheter, and the physiological information for the internal body surface is determined using at least some of the catheter potentials.

17 Claims, 7 Drawing Sheets (51) Int. Cl.
*A61B 5/00* (2006.01)
*A61B 5/01* (2006.01)
*A61B 18/14* (2006.01)
*A61B 18/00* (2006.01)

(52) U.S. Cl.
CPC .......... *A61B 5/0422* (2013.01); *A61B 5/6852* (2013.01); *A61B 5/015* (2013.01); *A61B 18/1492* (2013.01); *A61B 2018/00839* (2013.01)

(56) References Cited

U.S. PATENT DOCUMENTS

2009/0253976 A1   10/2009   Harlev et al.
2014/0278129 A1   9/2014    Voth et al.

OTHER PUBLICATIONS

Barr, Roger C., et al., "Relating Epicardial to Body Surface Potential Distributions by Means of Transfer Coefficients Based on Geometry Measurements", IEEE Transactions on Biomedical Engineering (vol. BME-24, Issue: 1, Jan. 1977), (Jan. 1977), 1-11.

"International Application No. PCT/NZ2016/050024, International Search Report and Written Opinion dated Jun. 9, 2016", (Jun. 9, 2016), 17 pgs.

Brooks, Anthony G., et al., "Outcomes of long-standing persistent atrial fibrillation ablation: A systematic review", Heart Rhythm, vol. 7, No. 6, Jun. 2010, (Jun. 2010), 835-846.

Narayan, Sanjiv M., et al., "Treatment of Atrial Fibrillation by the Ablation of Localized Sources: The Conventional Ablation for Atrial Fibrillation With or Without Focal Impulse and Rotor Modulation (CONFIRM) Trial", J Am Coll Cardiol. Aug. 14, 2012; 60(7): 628-636, (Aug. 14, 2012), 628-636.

Wang, Yong, et al., "Application of the Method of Fundamental Solutions to Potential-based Inverse Electrocardiography", Annals of Biomedical Engineering, Aug. 2006; 34 (8), 1272-88, (Aug. 2006), 1272-1288.

HEART MAPPING SYSTEM

PRIORITY CLAIM TO RELATED APPLICATIONS

This application is a U.S. national stage application filed under 35 U.S.C. § 371 from International Application Serial No. PCT/NZ2016/050024, which was filed 19 Feb. 2016, and published as WO2016/133409 on 25 Aug. 2016, and which claims priority to U.S. Provisional Application No. 62/118,395, filed 19 Feb. 2015, and to New Zealand Application No. 705231, filed 19 Feb. 2015, which applications and publication are incorporated by reference as if reproduced herein and made a part hereof in their entirety, and the benefit of priority of each of which is claimed herein.

FIELD OF THE INVENTION

The present invention relates to the determination of physiological information or activation maps of surfaces within the human body, such as chambers of the heart. In particular the invention relates to an improved method of determining physiological information using a catheter.

In particular, the present invention relates to real-time mapping of electrical activity on the inner or endocardial surface of chambers of the heart. Further, the invention provides an improved method for constructing such maps using intracardiac catheters containing multiple electrodes.

BACKGROUND

Electro-anatomic mapping is now widely used to guide treatment of heart rhythm disturbances. This involves the following steps i) 3D heart surface geometry is reconstructed for the chamber (or chambers) of concern ii) electrical signals (time varying electric potentials) are recorded at a number of registered points on the heart surface, and iii) electrical activity throughout the region is rendered, in time and space. Based on this information, likely sources of rhythm disturbance in the heart wall are then located and ablated.

Atrial fibrillation (AF) is the most common heart rhythm disturbance and its prevalence increases with age and heart disease. AF impairs exercise performance, may cause discomfort and increases the risk of stroke. The long-term success of treating persistent and permanent AF with conventional electro-anatomic mapping and ablation methods has been disappointing, see Brooks A G, Stiles M K, et al. *Heart Rhythm.* 2010; 7:835-846.

For example, the widely used CARTO (Biosense Webster, Inc.) mapping system sequentially records electrical activity and 3D coordinates at individual points across the endocardial surface of a heart chamber. This enables reliable electro-anatomic maps to be reconstructed when electrical activity is repetitive, but not in persistent or permanent AF when spatio-temporal electrical activity is highly variable.

This has driven recent development of methods for near real-time mapping and analysis of electrical activity in persistent and permanent AF using intracardiac catheters that record electrical activity simultaneously at multiple 3D locations. In this setting, real-time covers acquisition, analysis and visualization processes that are completed within a few seconds at most.

One approach here is to use flexible multi-electrode basket catheters that make direct contact with the atrial surface. Electrical activity can be mapped throughout the cardiac cycle provided that electrodes remain in contact with the chamber wall and their 3D position is known.

The Constellation catheter (Boston Scientific, Inc.) is an expandable basket catheter with 64 electrodes to record potentials. Constellation catheters in a contact mapping system have detected rotors (or focal drivers) in patients with AF for the first time and almost doubled the success rate of catheter ablations by targeting rotor circuits directly [Narayan S M, Krummen D E, et al. *JACC.* 2012; 60:628-636-846]. This has led to the development of improved catheter design and novel phase mapping software by Topera Medical, Inc.

However, such contact mapping approaches have a number of inherent limitations. For successful real-time mapping across a complete atrial chamber, catheter dimensions need to be matched to those of the chamber of interest. Even if this can be done, the complexity of atrial anatomy means that some regions cannot be mapped adequately. Basket catheters with dimensions appropriate for global atrial mapping cannot easily be introduced into the atrial appendages or into the junctions of the pulmonary veins. Furthermore, a significant number of electrodes will not make good contact with the chamber wall throughout the cardiac cycle, which further limits anatomic resolution. Finally, the presence of a large basket catheter in an atrial chamber constrains deployment and positioning of other devices such as ablation catheters.

An alternate approach is to use noncontact mapping methods. Here, electrical activity is measured on a surface adjacent to the inner or outer surface of the cardiac chamber of interest and is then mapped onto the heart surface in question using inverse problem techniques. St. Jude Medical, Inc. markets a catheter and mapping system intended for noncontact 3D electro-anatomic mapping. The catheter consists of a 64-electrode array mounted on an inflatable balloon, but this device is not widely used for mapping AF. Reasons for this are that the closed balloon partially occludes the atrial chamber. Also, the electrodes on the balloon are often too far from the atrial wall for accurate reconstruction of surface activation (atrial dilatation is common in longstanding persistent AF).

Acutus Medical, Inc. is developing a complete mapping system based on an expandable basket catheter that contains 42 electrodes as well as ultrasound probes. With this approach, electrical activity recorded with a multi-electrode basket catheter in an atrial cavity is used to estimate an equivalent electrical dipole distribution within the atrial wall. A weakness of this approach is that the distribution is an inferred measure that cannot be equated directly with the surface potentials measured by clinicians during the ablation process. Furthermore, the low channel count constrains the spatial resolution that can be achieved and the dimensions of the catheter preclude its use in the atrial appendages or pulmonary vein junctions.

CardioInsight Technologies, Inc. maps electrical activity measured on the body surface with a multi-electrode vest onto the epicardial surface of the heart using an inverse method. The approach is non-invasive, but it requires accurate 3D anatomic representations of body surface and epicardial geometry using computed tomography (CT) or magnetic resonance imaging (MRI). Weaknesses include the lack of spatial resolution in mapping atrial electrical activity and the fact that the epicardial electrical activity reconstructed with this approach cannot be directly related to the endocardial activity recorded by clinicians during AF ablation.

OBJECTS OF THE INVENTION

It is an object of the invention to provide a new method of determining physiological information for an internal body surface, such as an endocardial surface, which will at least go some way to overcoming disadvantages of existing systems, or which will at least provide a useful alternative to existing systems.

It is an object of the invention to provide a new method of determining physiological information of an endocardial surface which will improve the accuracy of the physiological information and/or reduce the computation required to determine the physiological information.

Further objects of the invention will become apparent from the following description.

SUMMARY OF INVENTION

In one aspect the invention describes a method of determining physiological information for an internal body surface using an open catheter comprising multiple sensors, the method comprising the steps of:
  a) obtaining sensor potentials using a plurality of the multiple sensors,
  b) determining catheter potentials within the catheter from the sensor potentials, and
  c) determining the physiological information for the internal body surface using at least some of the catheter potentials.

A method as claimed in claim 1 wherein determining the catheter potentials comprises to performing a forward solution to a system of differential equations.

Preferably determining the physiological information for the internal body surface comprises solving a further set of differential equations.

Preferably the step of determining the physiological information for the internal body surface comprises using the catheter potentials to provide boundary conditions.

Preferably the step of determining the physiological information for the internal body surface comprises determining an inverse solution to the further set of differential equations.

Preferably the multiple sensors define a virtual catheter surface and the catheter potentials are determined in a volume within the catheter surface.

Preferably the method further comprises a step of interpolating the sensor potentials across at least part of the catheter surface.

Preferably the method includes meshing points on the catheter surface and the internal body surface.

Preferably the method further comprises meshing a greater number of points on the catheter surface than on the internal body surface.

Preferably the sensors comprise electrodes.

Preferably the physiological information comprises electric potentials.

Preferably the internal body surface comprises and endocardial surface.

Preferably the endocardial surface comprises, at least in part, an atrium or ventricle.

Prefeably the physiological information comprises an electro-anatomical mapping.

Preferably a numerical method is approach is adopted to solving the differential equations.

Preferably the numerical approach includes any one or more of FEM, BM, M or MM.

Preferably the numerical approach is implemented using a processor.

Preferably the catheter comprises a flexible basket.

Preferably the method comprises positioning the catheter within a chamber bounded by the internal body surface.

Preferably the method comprises positioning the catheter proximal to a region of the internal body surface.

Preferably the method comprises positioning the catheter in a plurality of positions within a chamber bounded by the internal body surface.

Preferably the method comprises the step of locating the catheter in the first position to obtain a first image of the internal body surface, and at least one second position to obtain an improved image of a portion of the internal body surface.

Preferably the method comprises introducing the chamber into the body using a percutaneous technique.

In another aspect the invetion provides a system for determining physiological information for an internal body surface, the system comprising:
  a) a catheter adapted to be inserted into a bodily chamber bounded by at least part of the internal body surface,
  b) a processing means operable to receive date relating to electric potentials sensed by the catheter and implement the method according to any one of claims 1 to 17.

Preferably the catheter comprises a flexible basket.

Accordingly in another aspect the invention may broadly be said to consist in a method of determining the physiological information of an endocardial surface using an open catheter comprising multiple electrodes and defining a catheter surface, the method comprising the step of:
  determining physiological information throughout the volume inside the catheter surface using data recorded on the multiple electrodes to provide boundary conditions for a system of differential equations.

This in turn increases the number of unique boundary conditions available for solution of a second set of differential equations that maps physiological information from the catheter onto the endocardial surface enabling efficient and robust inverse mapping not possible using other approaches.

Preferably the endocardial surface comprises, at least in part, an atrium or ventricle.

Preferably the physiological information comprises electrical information such as electric potentials.

Preferably the physiological information comprises an electro-anatomical mapping.

Preferably the method includes the step of determining the physiological information within the catheter surface is performed by a forward solution to a system of differential equations.

Preferably the solution is determined using a numerical method. Preferably the numerical approach is any one or more of FEM, BEM or meshless method (MM).

Preferably the method is implemented on a processor.

Preferably the open catheter comprises a flexible basket.

Preferably the multiple electrodes are arranged so as to provide substantially even coverage over the catheter surface.

Preferably the method includes the step of interpolating the electrode measurements across the surface of the catheter.

Preferably the system of differential equations comprises Laplace's equation.

Preferably the method comprises the step of determining the physiological information of the endocardial surface by finding an inverse solution to a system of differential equations with an unknown boundary condition at the endocardial surface and a boundary condition of the rate of flow normal to the catheter surface.

Preferably the method includes the step of selecting a ratio between determination points on the catheter surface and the endocardial surface.

Preferably the method includes the step of meshing a greater number of points on the catheter surface than the endocardial surface.

Preferably the method comprises the step of positioning the catheter within the endocardial surface.

Preferably the method comprises the step of positioning the catheter proximal to the endocardial region of primary interest.

Preferably the method comprises the step of positioning the catheter in a plurality of positions within the endocardial surface.

Preferably the method comprises the step of locating the catheter at a first position to obtain a global image of the endocardial surface and at least one second position to obtain an improved image of a portion of the endocardial surface.

Preferably the method will be used with an open catheter that can be introduced into a heart chamber using percutaneous techniques.

Preferably the open catheter comprises a plurality of electrodes.

Preferably the open catheter comprises a flexible basket that is able to be set in a plurality of shapes and dimensions.

Preferably the plurality of electrodes are arranged so as to provide substantially even coverage over the catheter surface.

Preferably the catheter comprises a means that enables it to be moved readily within the heart chamber.

Preferably the method includes the step of estimating and characterizing the potential field in the volume bounded by the open catheter using a forward solution of a system of differential equations.

Preferably the differential equations are consistent with Laplace's law.

Preferably the catheter may characterise features of the potential field inside the catheter including one or more of local potentials and potential gradients (which directly reflect current flow).

Preferably the method comprises the step of interpolating the potentials measured at electrodes on the open catheter across the closed surface defined by those electrodes.

Preferably the forward solution will be determined using a numerical method that will be implemented on a processor.

Preferably the method comprises the step of estimating the potential field on the endocardial surface of the heart chamber by finding an inverse solution to a system of differential equations consistent with Laplace's law with unknown boundary values at the endocardial surface of the heart chamber using information on the potential field within the volume bounded by the catheter.

Preferably the inverse solution will be determined using a numerical method. Preferably the numerical method is any one or more of FEM, BEM or MM.

Preferably the method will be implemented on a processor.

Preferably the endocardial potentials reconstructed using this method will be displayed on a computer graphics representation of the 3D geometry of the heart chamber.

Preferably the method comprises the step of positioning the catheter in the heart chamber. Preferably the method comprises the step of positioning the catheter in a plurality of positions within the heart chamber.

Preferably the method comprises the step of locating the catheter at a first position to obtain a global image of the endocardial surface and at least one second position to obtain a more accurate estimate of potentials on a portion of the endocardial surface.

Accordingly in a further aspect the invention may broadly be said to consist in a method of determining the physiological information of an endocardial surface from the readings of an open catheter comprising multiple electrodes and defining a catheter surface, the method comprising the steps of:
 a) calculating the forward solution for the physiological information inside the catheter surface, and
 b) calculating boundary condition information from the calculated forward solution.

Accordingly in a further aspect the invention may broadly be said to consist in a method of identifying regions of an endocardial surface having physiological abnormalities, the method comprising the steps of:
 a) measuring a plurality of electrical signals on a surface (defined by the electrode locations) inside the endocardial surface,
 b) calculating a plurality of normal rates of flow perpendicular to the surface using a forward solution to a set of differential equations and
 c) computing the physiological information at the endocardial surface using the electrical signals and/or the normal rates of flow.

Preferably the method further comprises displaying the computed physiological information on a cardiac image.

Accordingly in a further aspect the invention may broadly be said to consist in a method for determining the physiological information of an endocardial surface, the method comprising the steps of:
 a) Inserting an open catheter into a cavity at least partly bounded by the endocardial surface,
 b) Measuring physiological information at a plurality of points on the catheter,
 c) Determining additional physiological information at the surface of the catheter by determining physiological information inside the catheter, and
 d) Determining physiological information at an endocardial surface by solving a differential equation in the region between the catheter surface and the endocardial surface.

Accordingly in a further aspect the invention may broadly be said to consist in a method of determining the physiological information of an endocardial surface from the readings of an open catheter comprising multiple electrodes and defining a catheter surface, the method comprising the step of calculating the forward solution to a system of differential equations within the catheter surface.

Accordingly in a further aspect the invention may broadly be said to consist in a system for determining physiological information on an internal body surface the system comprising:
 a) a catheter adapted to be inserted into a bodily chamber, the catheter having a plurality of sensors adapted to measure physiological information,
 b) a processing means for receiving information from the plurality of sensors and processing the information into physiological information of a flow rate at the catheter surface,
 c) a processing means for receiving the information of the flow rate at the catheter surface and processing the information into physiological information of the physiological information of the endocardial surface.

Accordingly in a further aspect the invention may broadly be said to consist in a system for determining physiological information on an internal body surface the system comprising:
a) a catheter adapted to be inserted into a bodily chamber, the catheter having a plurality of sensors adapted to measure physiological information,
b) a processing means for receiving information from the plurality of sensors and processing the information into physiological information within the catheter,
c) a processing means for receiving the information of the physiological information within catheter and processing the information into physiological information of the internal body surface.

Preferably the system comprises a means of calculating the position of the catheter.

Preferably the position is relative to the endocardial surface.

Preferably the system comprises a means of generating a representation of the endocardial surface.

Preferably a processing means receives the position of the catheter and processes the position of the catheter surface relative to the endocardial surface.

Preferably the system comprises a means of calculating 3D positions of electrodes on the catheter. Preferably these positions are given relative to the endocardial surface of the heart chamber.

Preferably the system comprises a means of generating a representation of the endocardial surface of the heart chamber. Preferably a processing means receives the position of electrodes on the catheter and reconstructs the position of the catheter surface relative to the endocardial surface of the heart chamber.

Preferably the system comprises a means of estimating the spatial resolution of potentials estimated at specific points on the endocardial surfaces of the heart chamber.

Preferably the system comprises a means of accounting for potential error in potentials estimated at specific points on the endocardial surfaces of the heart chamber as a result of heart wall motion.

Preferably the system comprises a means of further spatio-temporal processing of the potentials estimated at specific points on the endocardial surfaces of the heart chamber so that drivers of AF and substrates that sustain AF can be identified. Features of such post-processing applications include: spatial and temporal filtering, activation time analysis, regional variability analysis, regional frequency analysis and phase mapping.

Accordingly in a further aspect the invention may broadly be said to consist in a method of determining electric potentials of an endocardial surface of a heart chamber using an open catheter comprising multiple electrodes, the method comprising the steps of:
a) obtaining electrode information using a plurality of the multiple electrodes,
b) determining catheter physiological information within the open catheter from the electrode information, and
c) determining the electrical potentials of the endocardial surface using at least some of the catheter physiological information.

Preferably the step of determining the electric potentials also uses at least some of the electrode information.

Preferably the catheter physiological information comprises catheter potentials.

Preferably the electrode information comprises electrode potentials.

Preferably the catheter is an expandable basket catheter that is open such that blood can pass freely through it, but where the multiple electrodes define a closed three dimensional surface.

Preferably the method includes the step of estimating potentials within a volume bounded by the catheter from potentials recorded at the multiple electrodes.

Preferably the method further includes the step of using recorded potentials and potentials estimated within the catheter to reconstruct potentials on the endocardial surface or a region of the endocardial surface.

Accordingly in a further aspect the invention may broadly be said to consist in a method of determining electrical potentials on an internal body surface using an open catheter comprising multiple electrodes, the method comprising the steps of:
a) obtaining electrode potentials using a plurality of the multiple electrodes,
b) determining catheter potentials within the catheter from the electrode potentials, and
c) determining the electrical potentials of the internal body surface using at least some of the catheter potentials.

Preferably the step of determining the electrical potentials also uses at least some of the electrode potentials.

Alternatively the step of determining the electrode potentials uses potentials close to but not on the electrodes.

Preferably the internal body surface may be the heart, gut or bowel.

Preferably the catheter is an expandable basket catheter that is open such that body fluids can pass freely through it, but where the multiple electrodes define a closed three dimensional surface.

Preferably the method comprises the steps of:
a) obtaining the geometry of the internal body surface,
b) obtaining the position of the catheter within the internal body surface,
c) using at least some of the electrode, catheter and inner surface electrical potentials, geometry of the internal body surface and position of the catheter to create a visual representation of the internal body surface.

Preferably the method comprises the steps of:
a) positioning the catheter at a first location and obtaining a first plurality of electrode potentials
b) positioning the catheter at a second location and obtaining a second plurality of electrode potentials using a plurality of the multiple electrodes,
c) determining the electrode potentials of the internal body surface using at least some of the first and second pluralities of electrode potentials.

Preferably at least one of the first or second pluralities of electrode potentials is a global mapping of the internal body surface.

Preferably at least one of the first or second pluralities of electrode potentials is a more accurate map of a region of the internal body surface.

Preferably at least one of the first or second locations is a substantially central location in the internal body surface.

Preferably at least one of the first or second locations is substantially closer to a region of interest than the other location.

Preferably pluralities of electrode potentials are obtained at plurality of locations.

Preferably an operator can direct the location of the catheter to a desired location to obtain a set of electrode potentials.

Accordingly in a further aspect the invention may broadly be said to consist in a method of mapping the endocardial surface of the heart chamber using a catheter with multiple electrodes comprising the steps of:
- a) obtaining electrode potentials using a plurality of the multiple electrodes,
- b) determining catheter potentials within the catheter from the electrode potentials,
- c) determining endocardial surface electrical potentials using at least some of the electrode potentials and at least some of the catheter potentials,
- d) obtaining the geometry of the heart chamber,
- e) obtaining the position of the catheter within the heart chamber, and
- f) using at least some of the electrode, catheter and endocardial surface electrical potentials, geometry of the heart chamber and position of the catheter to create a visual representation of the heart chamber.

Preferably a processor is configured to carry out any one or more of the steps.

A non-transitory storage medium having machine-readable instructions stored thereon, that when executed by a processor cause the processor to perform the method claimed in any one of the previous embodiments.

Where suitable the preferable aspects of the system may be applied to any one or more of the embodiments described.

The disclosed subject matter also provides method or system which may broadly be said to consist in the parts, elements and features referred to or indicated in this specification, individually or collectively, in any or all combinations of two or more of those parts, elements or features. Where specific integers are mentioned in this specification which have known equivalents in the art to which the invention relates, such known equivalents are deemed to be incorporated in the specification.

Further aspects of the invention, which should be considered in all its novel aspects, will become apparent from the following description.

DRAWING DESCRIPTION

A number of embodiments of the invention will now be described by way of example with reference to the drawings in which.

DETAILED DESCRIPTION OF THE DRAWINGS

Throughout the description like reference numerals will be used to refer to like features in different embodiments.

In an embodiment the system provides a means of reconstructing panoramic electrical activity in a heart chamber from physiological information, most particularly, time-varying electrical potentials (which may also be referred to as electrical fields or simply, fields) recorded using an open catheter inside the chamber that contains multiple sensors which may comprise electrodes, some or all which are not in contact with the wall of the chamber. A numerical approach is used to estimate physiological information (most preferably electrical potentials, electrical fields, or fields) in the volume bounded by the electrodes from the recorded potentials. This provides the additional boundary conditions necessary for accurate inverse mapping of potentials onto the inner surface of the heart chamber. For instance, in inverse solution packages that employ Boundary Element Methods (BEMs), it is necessary to specify both potential and potential gradients at measurement points.

This system enables rapid reconstruction and visualisation of electrical potentials on an internal body surface, particularly an internal surface bounded by a chamber such as the endocardial surface of a cardiac chamber, or region of that chamber. Theses potentials comprise physiological information and are preferably from electrical potentials which may be measured with an expandable multi-electrode basket catheter, in which either all or some of the electrodes are not in contact with the surface. Such a catheter is open in a sense that bodily fluid such as blood within the chamber passes freely through it, but in which the electrodes define a mathematically closed 3D surface.

It is anticipated that the system or methods disclosed could be used as the basis of a complete mapping system or alternatively to enhance the performance of existing or proposed systems.

Throughout the description like reference numerals will be used to refer to like features in different embodiments.

Figure 1:
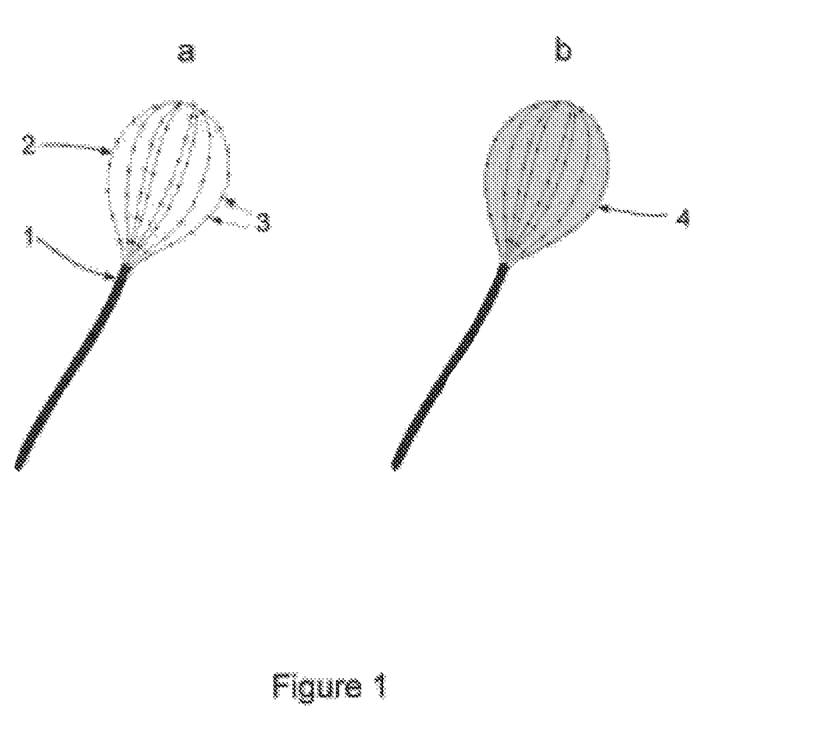
FIG. 1 is a schematic representation of (a) an open catheter with electrodes spaced along splines and (b) the closed virtual surface defined by the electrodes.

FIG. 1a shows a schematic representation of a multi-electrode mapping catheter 1. It consists of multiple expandable splines 2 with sensors or electrodes 3 spaced evenly along the splines. The catheter is open in the sense that fluid such as blood for example, can pass freely between the splines. However, as shown in FIG. 1b, all electrodes lie on a continuous virtual surface 4 that is closed in the mathematical sense.

Figure 2:
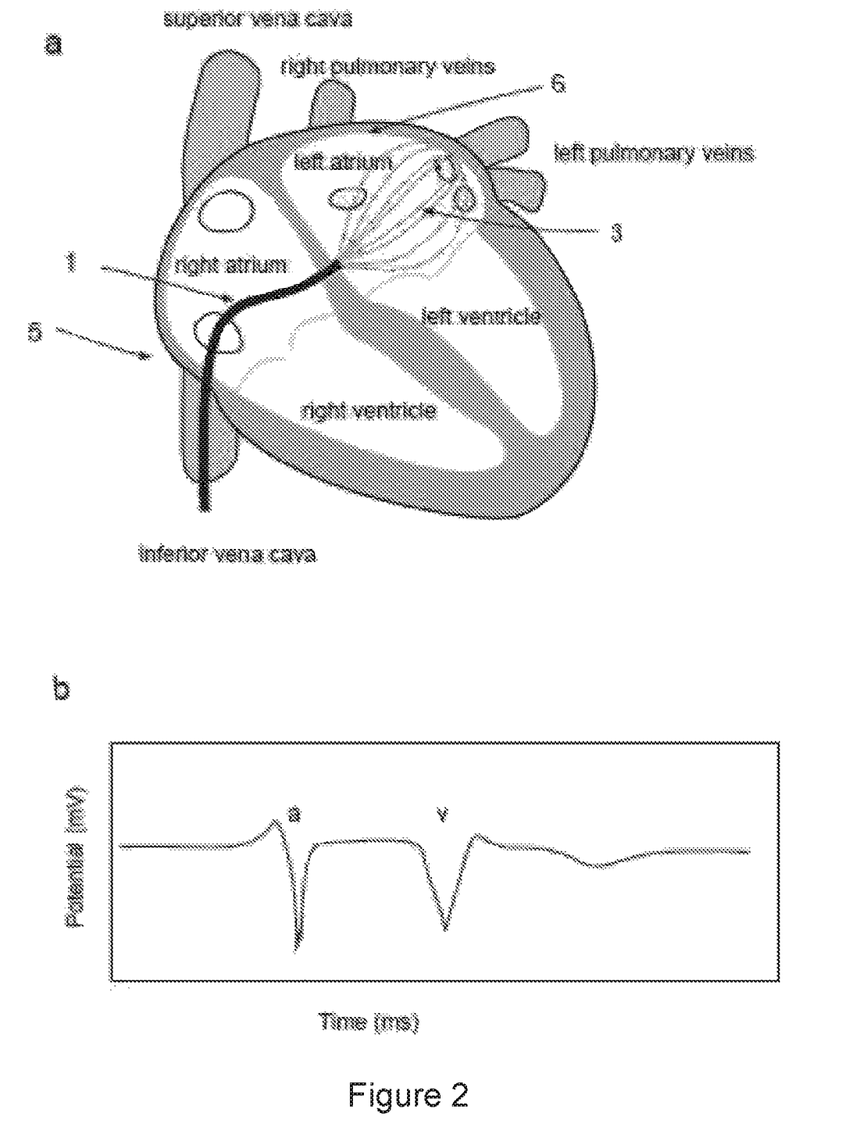
FIG. 2 is a schematic representation of a system embodiment showing (a) a catheter in the left atrium and (b) an atrial electrogram from one electrode.

FIG. 2a shows a schematic representation of the mapping problem in a heart 5. The catheter 1 is located in the left atrium (LA), and electrical potentials generated by electrical activity in the heart can be recorded by each of the multiple electrodes 3 simultaneously. An electrogram (potential as a function of time) at a typical electrode 3 is displayed for a single cardiac cycle in FIG. 2b. The potential distribution on the LA endocardial surface 6 at successive instants through the cardiac cycle must be reconstructed based on the corresponding potentials recorded at the multiple catheter electrodes. This typically involves an inverse approach, or solving an inverse problem. The objective of the inverse problem is to reconstruct source information (e.g. atrial endocardial potentials) from the measured field (e.g. potentials recorded at the catheter electrodes) based on a priori information on the physical relationships between sources and measured field. In this setting, information is also required about the 3D geometry of the endocardial surface and the 3D location of each of the electrodes.

In general, inverse problems are ill-posed because the number of independent degrees of freedom in the measured data are less than in the source field. Therefore, it is very difficult to obtain robust solutions to inverse problems. Measurement errors, for instance due to the presence of noise recorded by catheter electrodes and inaccuracy in the measurement of electrode positions and the representation of 3D endocardial surface geometry, are typically amplified in inverse solutions. There are well established methods for minimizing solution artefact (ie. Tikhonov regularization or L curve). Furthermore, solution robustness is increased when additional measured information is used.

FIG. 2a shows the four cardiac chambers: the left atrium (LA), right atrium (RA), right ventricle (RV) and left ventricle (LV). An endocardial surface 6 is typically at least part of the surface of one of the chambers of the heart. Where discussed herein the endocardial surface may be represented as a 2D surface, but it is understood that a user of the system would typically be investigating a 3D endocardial surface enclosing a chamber within. In some embodiments an endocardial surface may be only a portion of a chamber, that portion being of interest.

Assuming that there is no electrical source or sink in a volume ($\Omega$) inside a cardiac chamber that it is filled with blood and that blood has constant conductivity ($\sigma$) in all directions, the potential ($\phi$) throughout $\Omega$ may be described by a system of differential equations represented by the Laplace equation:

$$\nabla \cdot (\sigma \nabla \Phi) = 0 \text{ in } \Omega \quad \text{(Equation 1)}$$

A set of boundary conditions is necessary for solving a system of differential equations such as the Laplace equation. Dirichlet boundary conditions specify the values of a function on a boundary region. For instance $\phi$ may be specified on the virtual surface $\Gamma_c$ that bounds the electrodes on an open catheter:

$$\Phi = \Phi_0 \text{ at } \Gamma_c \quad \text{(Equation 2)}$$

On the other hand, Neumann boundary conditions set the normal derivative $\partial\Phi/\partial n$ of the function at a boundary. For instance at the surface of the catheter, $\Gamma_c$.

$$\frac{\partial \Phi}{\partial n} = C_0 \text{ at } \Gamma_c \quad \text{(Equation 3)}$$

Here n indicates the direction normal to the virtual surface $\Gamma_c$.

The appropriate boundary conditions to use will depend on the nature of the problem being solved. Dirichlet boundary conditions alone are not sufficient to solve the inverse problem represented in FIG. 2 in domains where Laplace's law applies.

In the most common solution of cardiac inverse problem, Green's second theorem is used to express a relationship that involves the cardiac and measurement surfaces only, see for example, Barr R C, et al. IEEE Transactions on Biomedical Engineering. 1977; 1:1-11, and these surfaces are discretized using the boundary element method (BEM). It is necessary to specify both Dirichlet and Neumann boundary conditions on the measurement surface to solve the inverse problem. This is not a problem if the measurement surface is non-conducting as is the case on the body surface or with multi-electrode balloon catheters, because $$\frac{\partial \Phi}{\partial n} = 0$$

at $\Gamma_c$ under these circumstances. However, current passes through an open multi-electrode catheter and therefore $$\frac{\partial \Phi}{\partial n} \neq 0$$

at $\Gamma_c$.

Although BEM is inherently accurate, it is difficult to use. Meshing of heart and measurement surfaces can be time-consuming and precise estimates of surface normals are required. Furthermore, the method can be unstable where regions of the measurement surface coincide with the cardiac surface as is the case when some electrodes on a mapping catheter make contact with the wall. This problem is due to the formation of singularities adjacent to measurement and cardiac surfaces, and must be dealt with as a special case. Meshless methods (MMs) that employ the Method of Fundamental Solutions (MFS) have been developed in other fields to overcome the problems of BEMs. This approach has also been used for inverse mapping of electrical activity in the heart from body surface potentials, see for example, Wang Y & Rudy Y. Annals of Biomedical Engineering. 2006; 34:1272-88.

MMs can be applied to the inverse problem represented in FIG. 2. A set of fictitious current sources (or sinks) is positioned on a boundary outside the cardiac surface and it is assumed that Laplace's law holds throughout the volume inside the boundary. Source magnitudes which give rise to potentials that best match potentials recorded on the catheter are then determined using standard inverse solution methods. Corresponding potentials on the cardiac surface are then estimated from these sources. MMs are both more efficient and more robust than BEMs in this setting. They are much simpler computationally, are far less reliant on accurate 3D descriptions of the endocardial geometry of the heart cavity and provide solutions when measurement points lie on the endocardial surface. Although MMs do not depend on the specification of both Dirichlet and Neumann boundary conditions on the measurement surface as is the case with BEM, the addition of accurate information relating to the potential field in the volume bounded by the catheter significantly improves the conditioning of the inverse problem.

In an embodiment, the method provides an accurate means of estimating potentials in the volume bounded by the electrodes from the potentials recorded at those electrodes. This is a key step toward meeting the overall objects of this invention, because it provides additional information that is necessary for robust solution of the inverse problem.

There are a number of possible ways of achieving this. For example the following steps can be followed:

i) A surface interpolation approach is employed to refine potentials at the virtual catheter surface 4 from the multiple electrodes 3 or recording locations.

ii) The forward problem (equation 1) is solved inside the catheter surface to obtain the internal potential field using measured and interpolated potentials on the virtual catheter surface as Dirichlet boundary conditions.

Because this forward problem is well posed and because it represents the physical relationships that determine current flux in the volume bounded by the electrodes faithfully, it provides the most accurate possible estimate of the potential field within this volume that can be obtained from the recorded potentials. The absolute accuracy depends on the extent to which the number and spacing of electrodes is sufficient to capture the complexity of the internal potential field.

Figure 3:
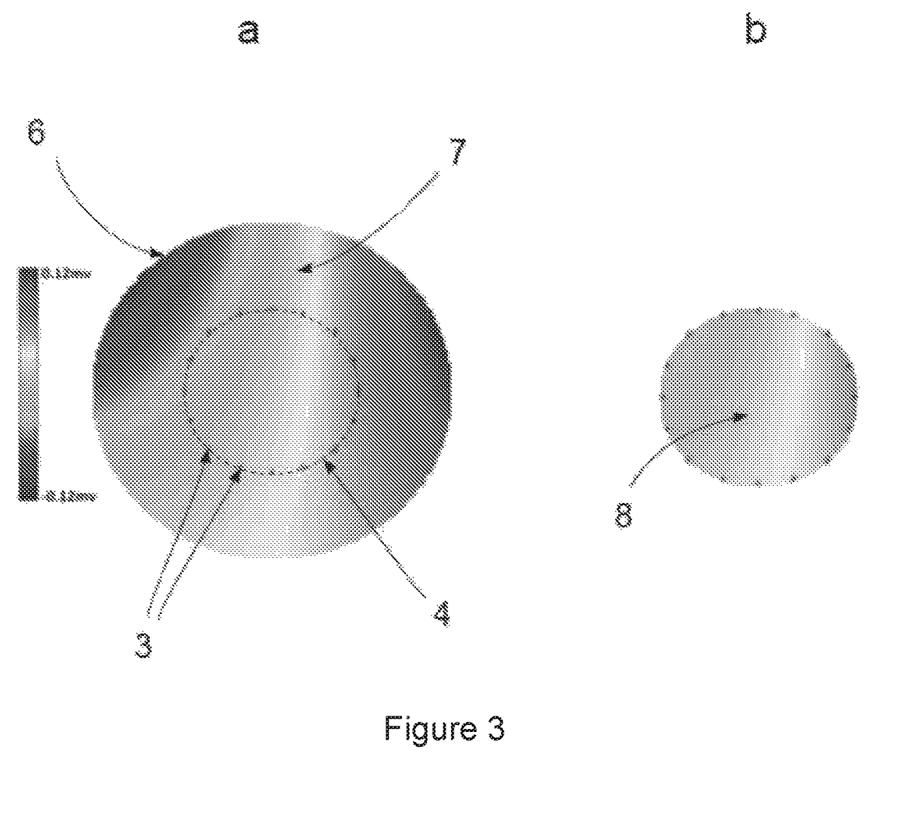
FIG. 3 shows steps of an embodiment of the method where (a) a representative potential distribution is sampled at internal points on a circle and (b) the potential distribution within the circle is reconstructed by a forward solution using potentials interpolated around the virtual inner circle from the sampled potentials.

FIG. 3 demonstrates this process using a two dimensional (2D) model. A representative potential field 7, generated within a simplified endocardial surface 6 in FIG. 3a, satisfies the 2D version of Laplace's law everywhere within that surface. A 2D representation of a catheter 2 has sixteen electrodes 3 evenly spaced around a virtual boundary 4, shown by a dotted line. Assuming that only the potentials at the electrodes 3 are known, potentials elsewhere around the boundary 4 can be interpolated. These provide the boundary conditions for solution of Laplace's equation inside the catheter. FIG. 3b shows the resultant inner potential field 8, which is indistinguishable from the initial field inside the catheter in FIG. 3a. The inner potential field 8 can be used to approximate potential gradients around the boundary providing the additional Neumann boundary conditions necessary for inverse solutions using BEM. In this example the potential field inside the virtual boundary was reconstructed by solving the forward problem using a finite difference method (FDM), but FEM and finite volume method FVM) discretizations can be used and may be more efficient where the topology of the virtual surface bounding the electrodes is complex.

While it is not necessary to specify Neumann boundary conditions on the electrode surface when MMs are used to solve the inverse problem, the inclusion of accurate potential estimates at points inside the virtual surface increases the robustness of the solution. Here the MFS can be used to reconstruct potentials at a distributed set of sample points in the volume bounded by the electrodes. While such meshless solutions of the forward problem are inherently less well-posed than with FDM, FEM and FVM, they are highly efficient and perform well in this setting.

In summary, application of the forward solution to obtain additional information about the potential field inside the catheter is a key step in obtaining robust subsequent solutions of the inverse problem. Reconstruction of the potential field inside the catheter enables estimation of the flux distribution throughout the volume as well as the potential gradients on the virtual surface defined by the electrodes. This rich set of additional information enables robust solutions of the inverse solution that have not previously been possible and it can be acquired using a variety of numerical methods. It provides the boundary data necessary for a range of numerical solutions of the inverse problem including FEMs, BEMs and MMs.

Figure 4:
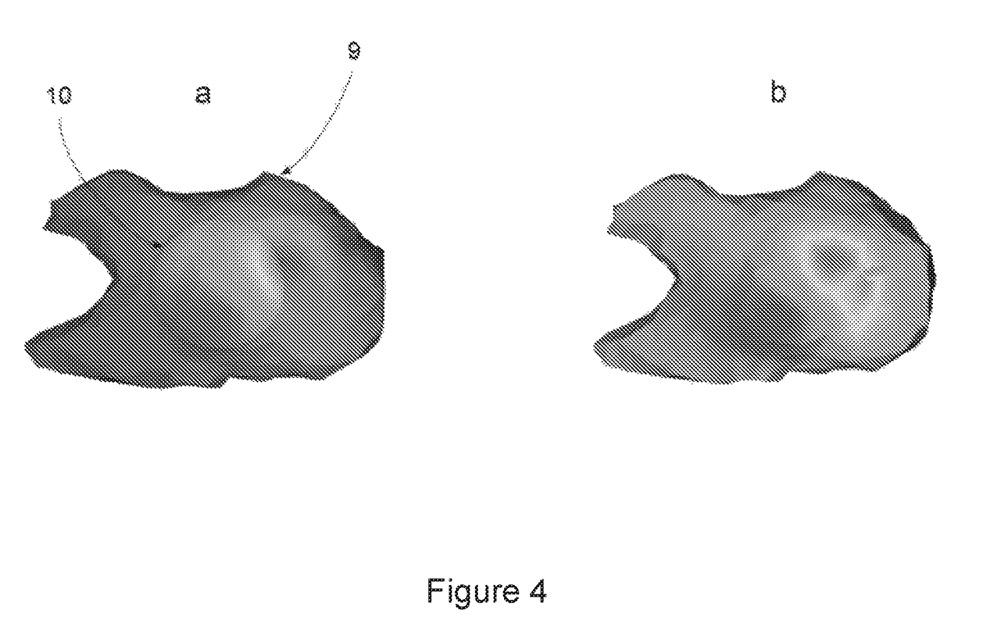
FIG. 4 shows an embodiment of the method where forward and inverse solutions are used in combination to reconstruct endocardial surface potentials from a set of potentials recorded inside a cardiac chamber. A representative potential field inside an atrial chamber (a) is sampled on an internal virtual sphere and a forward solution is used to reconstruct the potential field within it. Potentials on the endocardial surface (b) are then estimated by solving the inverse problem using the additional boundary information derived from the potential field inside the sphere.

FIG. 4 illustrates computational proof-of-concept investigations of the application of the method to mapping potentials recorded with a multi-electrode catheter onto the atrial endocardial surface. A representation of the 3D endocardial surface of the left atrium defines the LA chamber 9 and a 3D potential field which satisfies Laplace's law is generated throughout it. This potential is sampled at 64 uniformly-spaced points on the surface of a spherical surface 10, representing the electrodes on an open basket catheter. The potential field inside the sphere is estimated from the sampled potentials by solving the forward problem. Surface potentials across the spheherical surface 10 and corresponding normal potential gradients are then used as boundary values for solution of the inverse problem. Reconstructed endocardial potentials in FIG. 4b are compared with initial endocardial potentials in FIG. 4a by evaluating the correlation (CC) between them. In this case CC is 0.8.

Results of these investigations are as follows:

i) The method can reconstruct endocardial potentials that correspond closely to the original endocardial potentials and are acceptably robust in the presence of electrical noise.

ii) Larger catheters provide a more complete reconstruction of the global potentials on the atrial endocardial surface and 64 electrodes are sufficient under most circumstances.

iii) The method may not provide accurate reconstructions of local potentials in regions where endocardial geometry is complex, particularly when there is a high level of potential variation across the endocardial surface. Under these circumstances, a smaller catheter adjacent to region of interest faithfully reproduces local endocardial potentials.

Figure 5:
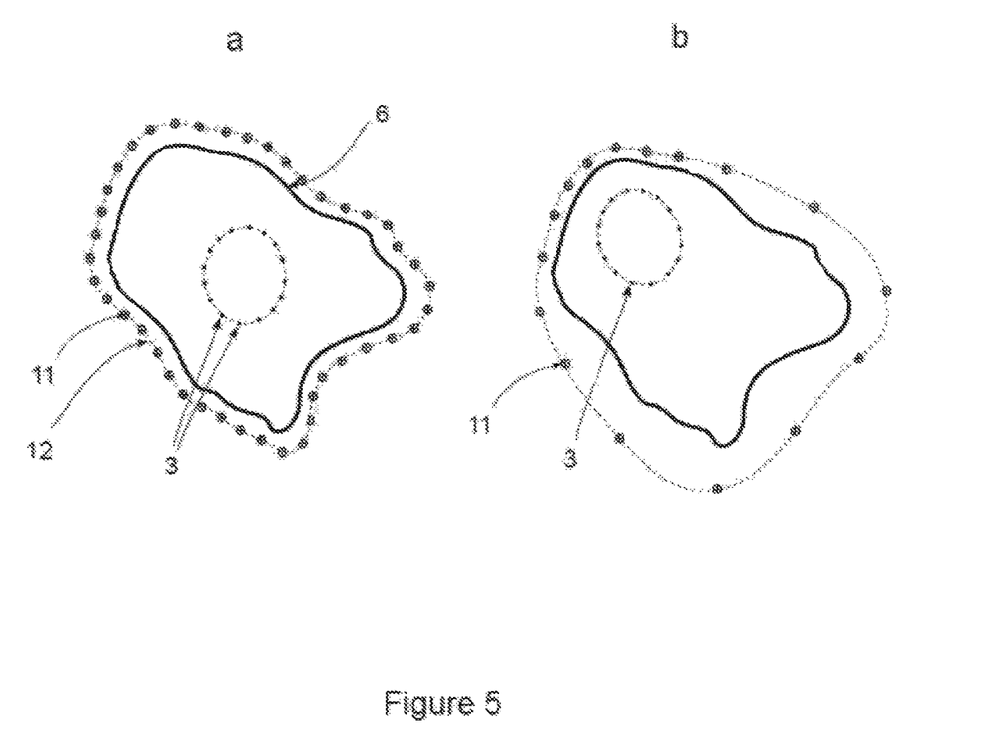
FIG. 5 shows an embodiment of the method where a meshless method is used to reconstruct endocardial potentials on an endocardial surface. In this approach, a restricted set of fictitious sources that best match the potential field sampled with an internal catheter and also estimated inside the catheter are mapped onto the endocardial surface (a). Adaptive source distribution (b) optimizes the number of unique sources and enables estimation of the spatial resolution of inverse endocardial surface reconstruction.

FIG. 5a illustrates how the inverse endocardial mapping problem is approached with MMs that use the MFS. In FIG. 5a a set of discrete fictitious sources 11 is positioned on a boundary 12 that contains the endocrdial surface 6 of the cardiac chamber. The fictitious sources are each fundamental solutions of Laplace's equation (equation 1 above) within the source-free volume $\Omega$ contained in the cardiac chamber. The potential $\phi_i$ at any point (x,y,z) in 3 due to a source i located on the boundary 2 is $$\phi_i(x, y, z) = \alpha_i + \frac{\beta_i}{r_i} \qquad \text{(Equation 4)}$$

where $r_i$ is the Euclidean distance between (x,y,z) and the source at $(x_i, y_i, z_i)$.

That is $r_i = \sqrt{(x-x_i)^2 + (y-y_i)^2 + (z-z_i)^2}$

The total potential $\Phi$ at any point in $\Omega$ contributed by a set of M fictitious sources is $$\Phi(x, y, z) = \sum_{i=1}^{M} \phi_i(x, y, z) \qquad \text{(Equation 5)}$$

Source densities $\beta_i$ are selected to best match potentials recorded at each of the electrodes on the catheter 4, but also potentials inside the catheter 5 estimated by solving the forward problem. Source densities are determined by solving inverse problem with appropriate regularization and endocardial surface potentials are then mapped using equation 5.

While optimal placement of fictitious sources is empirical to some extent, a number of relatively straightforward a priori rules apply. The number of independent fictitious sources is less than the degrees of freedom of the measured potential distributions as determined by singular value analysis. The distribution of sources on the fictitious boundary should be bound by this constraint and it should be adaptive—most dense where the measurements are closest to the cardiac surface and least dense here they are furthest from it. Where sources are sparse, the accuracy of inverse mapping is increased with displacement of the surface from the cardiac boundary and vice versa. Finally the displacement of the boundary should be sufficient to accommodate uncertainty in the representation of cardiac surface geometry.

FIG. 5b represents a method of distributing fictitious sources that is consistent with these rules. The number of independent sources 11 is equal to the number of electrodes 3 on the catheter and their spacing reflects the position of the catheter with respect to the wall. It is possible to add additional sources without loss of generality by interpolating along the fictitious boundary between independent source points.

The use of MMs in the setting above gives rise to computationally efficient inverse solutions that are marginally less accurate than BEM, but more robust in the presence of uncertainty about endocardial geometry and the relative position of measurement sites on the catheter with respect to the endocardial surface. Finally, the positioning of independent sources on the external boundaries provides direct feedback on the spatial resolution of potentials that are mapped onto the endocardial surface.

Figure 6:
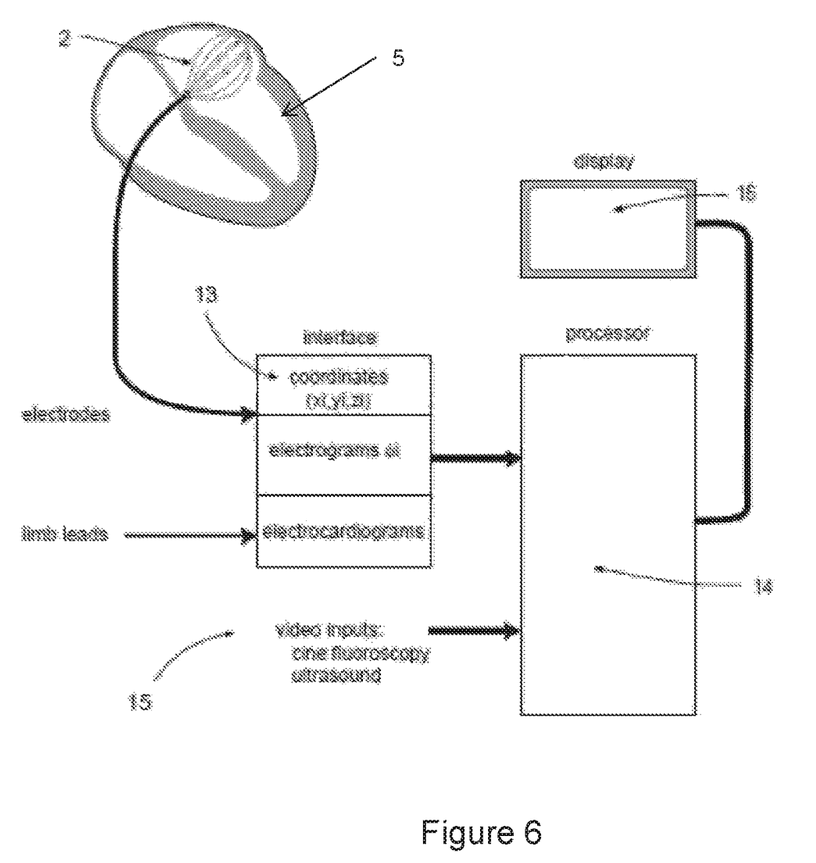
FIG. 6 shows a schematic diagram of a catheter in a heart and additional recording, control and processing devices that are required for inverse endocardial mapping.

FIG. 6 shows a diagram of the system in use. A catheter is placed inside a volume of interest, typically a heart chamber. Catheters are electrically connected to an interface 13, which is electrically isolated and may comprise a proprietary system or a set of such systems. Instantaneous potentials and the 3D positions are acquired from individual electrodes on one or more cardiac catheters. For instance potentials and 3D positions may be recorded simultaneously from multi-electrode basket catheters positioned in the RA and LA, or from a multi-electrode basket catheter and an ablation catheter in the same cardiac chamber. 3D electrode positions are recorded using impedance techniques, magnetic sensors, ultrasound sensors or combinations of these methods. Electrocardiograms (ECGs) are also acquired without position information for standard lead configurations.

The processing unit 14 controls the acquisition and processing of data so that recorded potentials or information derived from them can be mapped onto the endocardial surface of a heart chamber or chambers in a form that is useful to the operator. The processing unit is an electronic computing device with a real-time operating system and it may include a field programmable gate array (FPGA) and appropriate memory. It may be connected to the interface 13 either directly or wirelessly.

Alternative forms of the present invention may comprise a computer program or computer readable medium adapted to perform the method. The processor unit or means may comprise a microprocessor, FPGA, logic circuit or other form of processor. The processor means may be incorporated into a computer, for example a PC, mainframe, remote server or cloud-cluster. The processor means may be a single device or may interface with further processing means. Connections may be made between the processing means through a network or wired/wireless communications. The processor or processing means may receive information from a data storage device such as a removable storage disk, hard-disk, ROM, RAM or a network connection.

The first processing step is to construct a computer representation of the 3D endocardial surface geometry of the heart chamber or chambers of interest. This may be derived from i) cardiac MR images ii) contrast-enhanced cardiac CT images or iii) surface coordinates mapped under fluoroscopic guidance using a contact catheter. Alternately, geometry created in iii) can be merged with endocardial surfaces segmented from i) or ii). Preferably, static 3D models will be integrated with cine-fluoroscopic imaging or ultrasound imaging to provide estimates of heart wall motion. Provision for the import of such video data is indicated in 15.

Processing steps that will be carried out during the acquisition of data from a catheter or catheters include those described in relation to FIGS. 3, 4 and 5 above. For each time interval, a forward solution will be used to estimate potentials inside the catheter followed by an inverse solution that enables potentials to mapped onto the endocardial surface of the cardiac chamber or chambers. This will be repeated at successive intervals throughout a recorded data set.

Endocardial potentials will be rendered on a computer representation of the 3D surface of the heart chamber or chambers presented on a screen or display device 16 in a form that can be manipulated interactively by the operator. The location of catheter or catheters with respect to the heart wall will also be displayed. Electrograms at selected endocardial points (or at selected catheter electrodes) and selected ECG leads will be presented simultaneously in a moving window with an adjustable time base. It will also be possible to display a projection of unique source points onto the endocardial surface providing intuitive information on the spatial resolution of the inverse maps presented. Preferably the processing and display of time-varying endocardial potentials will be completed in real-time or near real-time.

These may include the following:
spatial and temporal filtering
activation time analysis
regional variability analysis
regional frequency analysis
phase analysis Preferably the results of the analysis steps listed will be mapped onto a representation of the 3D heart displayed in 11.

The processing steps may be implemented in hardware or software or a combination of these. The steps or instructions may be stored in computer readable media or memory including a hard disk, random access memory (RAM), read only memory (ROM) a removable storage disk or device or other storage media.

Figure 7:
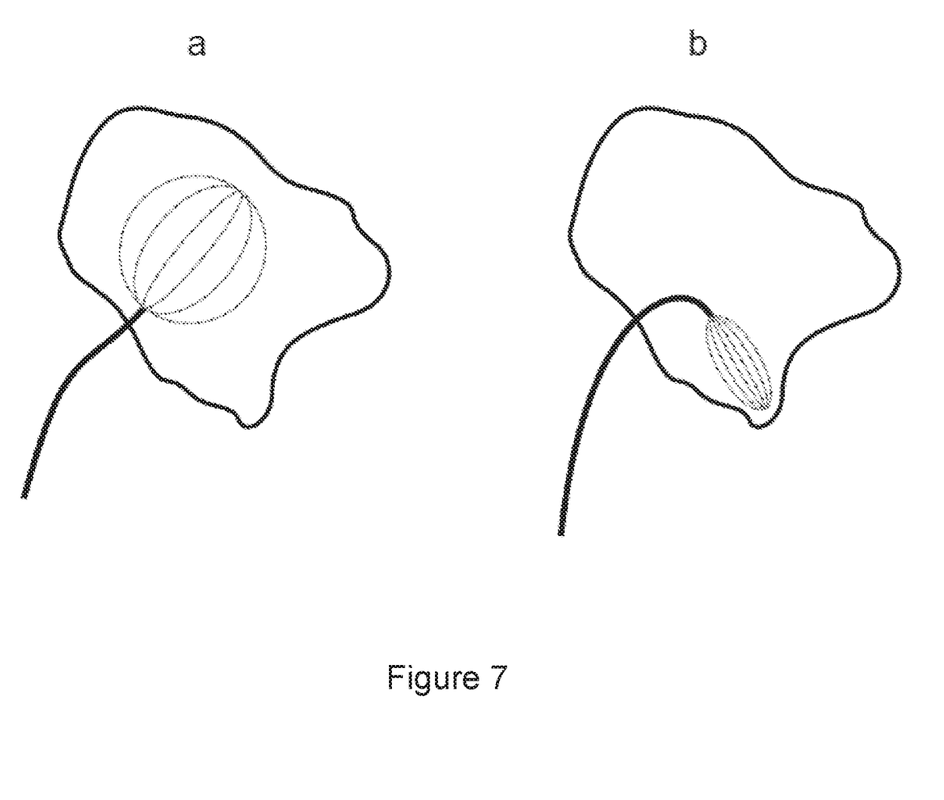
FIG. 7 shows a schematic diagram of an expandable catheter used in the open state for global panoramic mapping and in the closed state for region-of-interest mapping.

FIG. 7 shows a method of operating a catheter in a sequence of steps guided by the information displayed in 11 above. Initially a global picture of electrical activity on the endocardial surface of a heart chamber will be acquired and displayed. Preferably this will use a catheter positioned in a first position, generally centrally with electrodes in contact with or adjacent to as much of the endocardial surface of the heart chamber as possible. The catheter may be moved to one or more second positions to investigate regions of interest. FIG. 7a shows a catheter being used for global mapping. FIG. 7b shows how a catheter with smaller dimensions achieved, for example, by adjusting the size of the catheter may be used to map in specific regions of the chamber with greater precision, because it can be moved close to the endocardial surface.

In a preferred method a global mapping of electrical activity is obtained over a short period of time (for instance continuous periods of at least 10-20 seconds are required in AF) before a user decides which areas require further investigation. Higher resolution mappings will be obtained in these regions-of-interest by moving multi-electrode arrays with smaller diameters into them (again in AF continuous periods of at least 10-20 seconds are required for region-of-interest mapping). This method will support more efficient high-resolution endocardial mapping of electrical activity because it utilizes potentials recorded at all electrodes whether they are in contact with the endocardial surface of the heart chamber or not. The operator will also receive direct feedback the accuracy of endocardial maps through visual comparison of maps and electrograms displayed as the catheter is moved closer to the surface and as some electrodes make contact with it.

The mapping approach above could be carried out using combinations of catheters with different dimensions. Preferably a single adjustable catheter such as that shown in FIG. 7c will be used. Here the dimensions of the electrode array are altered by withdrawing or advancing the splines into or out of the catheter. Preferably the catheter will meet the following general specifications:

The catheter will be steerable.

It will be possible to lock the dimensions of the electrode array in multiple dimensions between fully open and fully closed states.

Electrodes will be uniformly spaced as far as is possible in open and closed states and distributed evenly across the mathematically closed virtual surface that bounds them.

Inter-electrode spacing will be sufficient to characterize electrical activity appropriately within endocardial regions on the order of 10 mm diameter.

Preferably it will be possible to introduce the catheter into atrial appendages and pulmonary vein in a closed state.

In summary combination of the processes illustrated in these figures provides an improved means of mapping endocardial electrical activity on a heart chamber or chambers. This is achieved, in part, by mapping potentials recorded on a catheter containing multiple electrodes back to the endocardial surface when some or all of the electrodes are not in contact with it (see FIG. 2). This involves the solution of an inverse problem that is inherently ill-posed. A desirable step in this process is solution of the forward problem inside the catheter (see FIG. 3), which provides additional information that improves the conditioning of the inverse problem enabling more robust solutions, independent of the method used. Proof-of-concept analysis (see FIG. 4) demonstrates that inverse mapping can be used to reconstruct global endocardial potentials provided the field inside the cardiac chamber is sampled sufficiently. However, local or region or interest (regional) mapping may be necessary to fully reconstruct endocardial surface potentials in regions where endocardial geometry is complex and/or there is rapid spatial variation of endocardial potentials. MMs can be used to reduce the scale of the inverse problem enabling acceptably rapid solution in the presence of relative motion of the electrodes and the heart wall (see FIG. 5). By combining appropriate systems for acquisition, processing and display of endocardial mapping data (see FIG. 6), with improved multi-electrode catheters, it is possible to provide more accurate, more rapid and more comprehensive results than with existing methods (see FIG. 7).

From the foregoing it will be seen that a method of determining physiological information of an endocardial surface is provided which improves the calculation of physiological information, for example, electrical potentials.

Unless the context clearly requires otherwise, throughout the description, the words "comprise", "comprising", and the like, are to be construed in an inclusive sense as opposed to an exclusive or exhaustive sense, that is to say, in the sense of "including, but not limited to".

Although this invention has been described by way of example and with reference to possible embodiments thereof, it is to be understood that modifications or improvements may be made thereto without departing from the scope of the invention. The invention may also be said broadly to consist in the parts, elements and features referred to or indicated in the specification of the application, individually or collectively, in any or all combinations of two or more of said parts, elements or features. Furthermore, where reference has been made to specific components or integers of the invention having known equivalents, then such equivalents are herein incorporated as if individually set forth.

Any discussion of the prior art throughout the specification should in no way be considered as an admission that such prior art is widely known or forms part of common general knowledge in the field.

The invention claimed is:

1. A method of determining physiological information for an internal body surface using an open catheter comprising multiple electrodes bounding a volume within the catheter, the method comprising:
   a) obtaining a first set of electric potentials using a plurality of the electrodes,
   b) determining a first set of boundary conditions from the first set of electric potentials,
   c) using the first set of boundary conditions to perform a forward solution to a first set of differential equations to provide a second set of electric potentials within the volume,
   d) determining a second set of boundary conditions from the second set of electric potentials,
   e) using the second set of boundary conditions to perform an inverse solution to a second set of differential equations, and
   f) determining the physiological information for the internal body surface using the inverse solution.

2. The method as claimed in claim 1 further comprising interpolating the first set of electric potentials.

3. The method as claimed in claim 1 wherein the physiological information comprises electric potentials on the internal body surface.

4. The method as claimed in claim 1 wherein the internal body surface comprises an endocardial surface.

5. The method as claimed in claim 4 wherein the endocardial surface comprises, at least in part, an atrium or ventricle.

6. The method as claimed in claim 1 wherein the physiological information comprises an electro-anatomical mapping.

7. The method as claimed in claim 1 further comprising using a numerical method to solve the first or second set of differential equations.

8. The method as claimed in claim 7 wherein the numerical method comprises any one or more of a finite element method, a boundary element method, or a meshless method.

9. The method as claimed in claim 7 wherein the numerical method is implemented using a processor.

10. The method as claimed claim 1 wherein the open catheter comprises a flexible basket.

11. The method as claimed in claim 1 further comprising positioning the catheter within a chamber bounded by the internal body surface.

12. The method as claimed in claim 11 further comprising positioning the catheter proximal to a region of the internal body surface.

13. The method as claimed in claim 12 further comprising positioning the catheter in a plurality of positions within the chamber.

14. The method as claimed in claim 12 comprising locating the catheter in a first position to obtain a first set of physiological information for a first portion of the internal body surface, and at least one second position to obtain a second set of physiological information for a second portion of the internal body surface.

15. The method as claimed in claim 1 further comprising introducing the catheter into the body using a percutaneous technique.

16. A system for determining physiological information for an internal body surface, the system comprising:
   a catheter adapted to be inserted into a bodily chamber bounded by at least part of the internal body surface, the catheter comprising multiple electrodes bounding a volume within the catheter, and
   a processor configured to:
   a) obtain a first set of electric potentials using a plurality of the electrodes;
   b) determine a first set of boundary conditions from the first set of electric potentials;
   c) use the first set of boundary conditions to perform a forward solution to a first set of differential equations to provide a second set of electric potentials within the volume;
   d) determine a second set of boundary conditions from the second set of electric potentials;
   e) use the second set of boundary conditions to perform an inverse solution to a second set of differential equations, and
   f) determine the physiological information for the internal body surface using the inverse solution.

17. The system as claimed in claim 16 wherein the catheter comprises a flexible basket.

* * * * *